United States Patent [19]
Rounbehler et al.

[11] Patent Number: 5,418,170
[45] Date of Patent: * May 23, 1995

[54] METHOD AND SYSTEM FOR SAMPLING AND DETERMINING THE PRESENCE OF SALTS OF AMMONIA AND AMINES IN CONTAINERS

[75] Inventors: David P. Rounbehler, Bedford; Eugene K. Achter, Lexington; David H. Fine, Sudbury; Freeman W. Fraim, Lexington, all of Mass.; Stephen J. MacDonald, Salem, N.H.; Helmut W. Klotzsch, Groton, Mass.

[73] Assignee: The Coca-Cola Company, Atlanta, Ga.

[*] Notice: The portion of the term of this patent subsequent to Oct. 4, 2011 has been disclaimed.

[21] Appl. No.: 51,209

[22] Filed: Apr. 22, 1993

Related U.S. Application Data

[63] Continuation-in-part of Ser. No. 019,908, Feb. 19, 1993, abandoned.

[51] Int. Cl.6 ............ G01N 21/76; G01N 35/02
[52] U.S. Cl. .................... 436/111; 436/172; 436/47; 422/80; 422/82.08; 209/3.1
[58] Field of Search ......... 436/47, 106, 43, 172, 436/111-113; 209/3.1; 422/80, 82.05, 82.08, 50, 93; 73/23.35

[56] References Cited

U.S. PATENT DOCUMENTS

| | | | |
|---|---|---|---|
| 4,094,780 | 6/1978 | Iwai et al. | 210/38 B |
| 4,174,633 | 11/1979 | Hoyt et al. | 73/432 R |
| 4,193,963 | 3/1980 | Bruening et al. | 422/52 |
| 4,485,669 | 12/1984 | Schmitt | 73/167 |
| 4,775,633 | 10/1988 | Rounbehler | 436/106 |
| 4,843,016 | 6/1989 | Fine | 436/106 |
| 4,880,120 | 11/1989 | Myers et al. | 209/3.1 |
| 4,914,964 | 4/1990 | Speiser | 73/865.9 |
| 5,152,963 | 10/1992 | Wreyford | 422/52 |
| 5,192,509 | 3/1993 | Surjaatmadja et al. | 422/75 |

*Primary Examiner*—James C. Housel
*Assistant Examiner*—Rachel Heather Freed
*Attorney, Agent, or Firm*—Birch, Stewart, Kolasch & Birch

[57] ABSTRACT

A method and system for injecting liquid into containers and for inspecting containers for the presence of certain substances such as potential contaminants such as ammonium salts or amine salts in glass or plastic bottles. A high speed system and method are provided for detecting these contaminants in these bottles. Ammonia and amines can be detected by chemiluminescence of samples of volatiles emitted from the bottles during the high speed inspection process. A solution of $Na_2CO_3$ is injected into the bottles in order to enhance the conversion of ammonium or amine salts to free ammonia or amines which are then released as vapors. This enhances the likelihood that a gas-phase detection system such as one using chemiluminescence detection techniques will detect the presence of contaminants containing ammonium salts or amine salts.

28 Claims, 6 Drawing Sheets

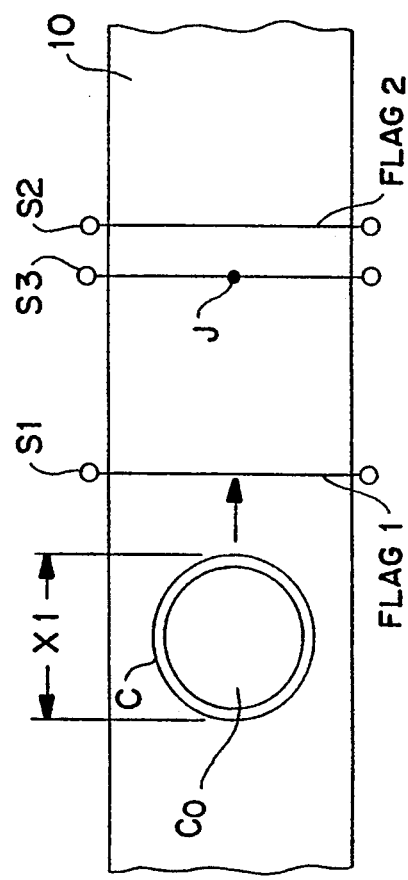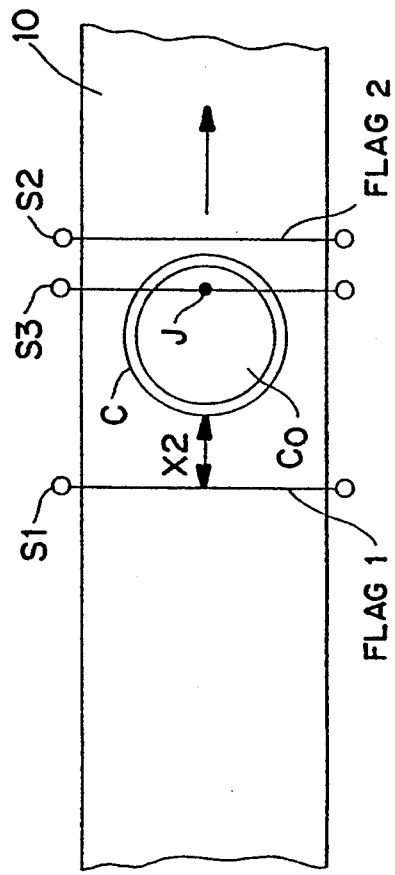

METHOD AND SYSTEM FOR SAMPLING AND DETERMINING THE PRESENCE OF SALTS OF AMMONIA AND AMINES IN CONTAINERS

BACKGROUND OF THE INVENTION

This application is a continuation-in-part of prior application Ser. No. 08/019,908 filed Feb. 19, 1993, now abandoned, by the same inventors and entitled the same, said prior application being assigned to the same assignee as the present application.

The present invention relates to liquid injection into containers and particularly to a container inspection system for sampling and determining the presence of certain substances, such as residues of contaminants of ammonium salts and amine salts within containers such as glass or plastic bottles. More specifically, the present invention relates to an improved sampling and analyzing system and method for determining the presence of residues of these contaminants in containers such as beverage bottles rapidly moving along a conveyor past a test station in a container sorting system.

In many industries, including the beverage industry, products are packaged in containers which are returned after use, washed and refilled. Typically refillable containers, such as beverage bottles, are made of glass which can be easily cleaned. These containers are washed and then inspected for the presence of foreign matter.

Glass containers have the disadvantage of being fragile and, in larger volumes, of being relatively heavy. Accordingly, it is highly desirable to use plastic containers because they are less fragile and lighter than glass containers of the same volume. However, plastic materials tend to absorb a variety of compounds which may later be desorbed into the product thereby potentially adversely affecting the quality of the product packed in the container. Examples of such compounds are ammonium salts, amine salts, ammonia, organic nitrogen compounds, and hydrocarbons including gasoline and various cleaning fluids.

SUMMARY OF THE INVENTION

Accordingly, it is a primary object of the present invention to provide a method and system for detecting the presence or absence of specific substances—e.g., contaminants of, or containing, ammonium salts or amine salts, in containers as the containers move rapidly along a conveyor on the way to or from a washer assembly or the like.

This and other objects of the present invention are fulfilled by providing a method of detecting the presence of ammonium salts or amine salts comprising the steps of providing an item such as a container, to be analyzed, adding an alkaline solution to the item to enhance liberation of vapors of ammonia and/or amines from the item and analyzing a sample including the vapors to determine the presence of ammonium salts or amine salts.

A preferred technique for analyzing the sample is to heat the sample obtained from the item to form nitric oxide (NO), mix the products of heating with a chemical reactant to generate a chemical reaction which causes chemiluminescence, and then to analyze radiation from the chemiluminescence to determine the presence or absence of ammonium and/or amine salts.

It is another aspect of the invention to provide a method and apparatus for rapidly injecting small amounts of liquid into containers (such as bottles) as the containers move rapidly along a conveyor at constant or variable speeds and spacings, substantially without spilling liquid over the outside of, or between, the containers. The liquid may be employed to enhance liberation of vapors from within the containers for detection of substances in the containers, or as additives, or for other purposes. In order that liquid not be spilled, the movements of each container is tracked with sensors upstream of a high speed injector, and one or more nozzles is timed to inject liquid in a narrow, high velocity stream only while the top opening of a container is under the nozzle(s).

The item may be a beverage container and the method may include the steps of rapidly injecting sodium carbonate ($Na_2CO_3$) to the container, displacing a portion of the container vapor contents to form a sample cloud at regions outside of the container adjacent the opening thereof, heating a portion of the sample cloud to convert ammonia and amines to NO, mixing the products of heating with ozone to generate a chemical reaction which causes chemiluminescence and optically analyzing the resulting radiation to determine the presence or absence of ammonium salts or amine salts in the container.

Another feature of the method of the present invention is to enhance the detection of vapors by rapidly injecting an aqueous solution of a chemical additive into the container through an opening therein to enhance liberation of vapors of ammonia or an amine, or both, from any ammonium salts and amine salts therein, said aqueous solution being injected at a sufficient velocity to displace a substantial portion of vapors so liberated towards a top region of said container; thereafter injecting a fluid through the opening to displace a portion of the vapors in the top region to regions outside of said container to form a sample cloud outside of the container adjacent the opening thereof; and analyzing a sample of the vapors in the sample cloud to determine the presence or absence of ammonia or amine(s) salts therein.

Still another aspect of the present invention is to provide a method for testing and verifying the proper operation of a system intended to detect the presence of ammonium salts and amine salts in an item, said system including an injection mechanism for adding a chemical additive from the group consisting of sodium carbonate, hydrated sodium carbonate, sodium tri-phosphate, potassium tri-phosphate and mixtures thereof to an item in order to change the pH of at least a portion of the item or its contents to a pH value of 9 or greater for enhancing liberation of vapors of ammonia or an amine or both from the item, and means for analyzing a sample including the vapors to determine the presence or absence of said ammonium or amine salts, comprising the steps of:

injecting a dye to the item with said injection mechanism, said dye being capable of changing color at about said pH value and said greater values; and detecting a change in color of the item as an indication of the presence of sufficient quantities of the chemical additive to cause said item to reach at least said pH value;

whereby the detection of the presence of said sufficient quantities of said chemical additive verifies the proper operation of the injection mechanism of the system thereof.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitative of the present invention and wherein:

FIG. 5 is a top plan diagrammatic view of a bottle moving left to right on a conveyor prior to moving through light beams and jets from an injector such as those of FIGS. 3 and 4;

FIG. 6 is a top plan diagrammatic view similar to FIG. 5 showing the bottle between the two light beams;

DETAILED DESCRIPTION OF PREFERRED EMBODIMENTS

Figure 1:
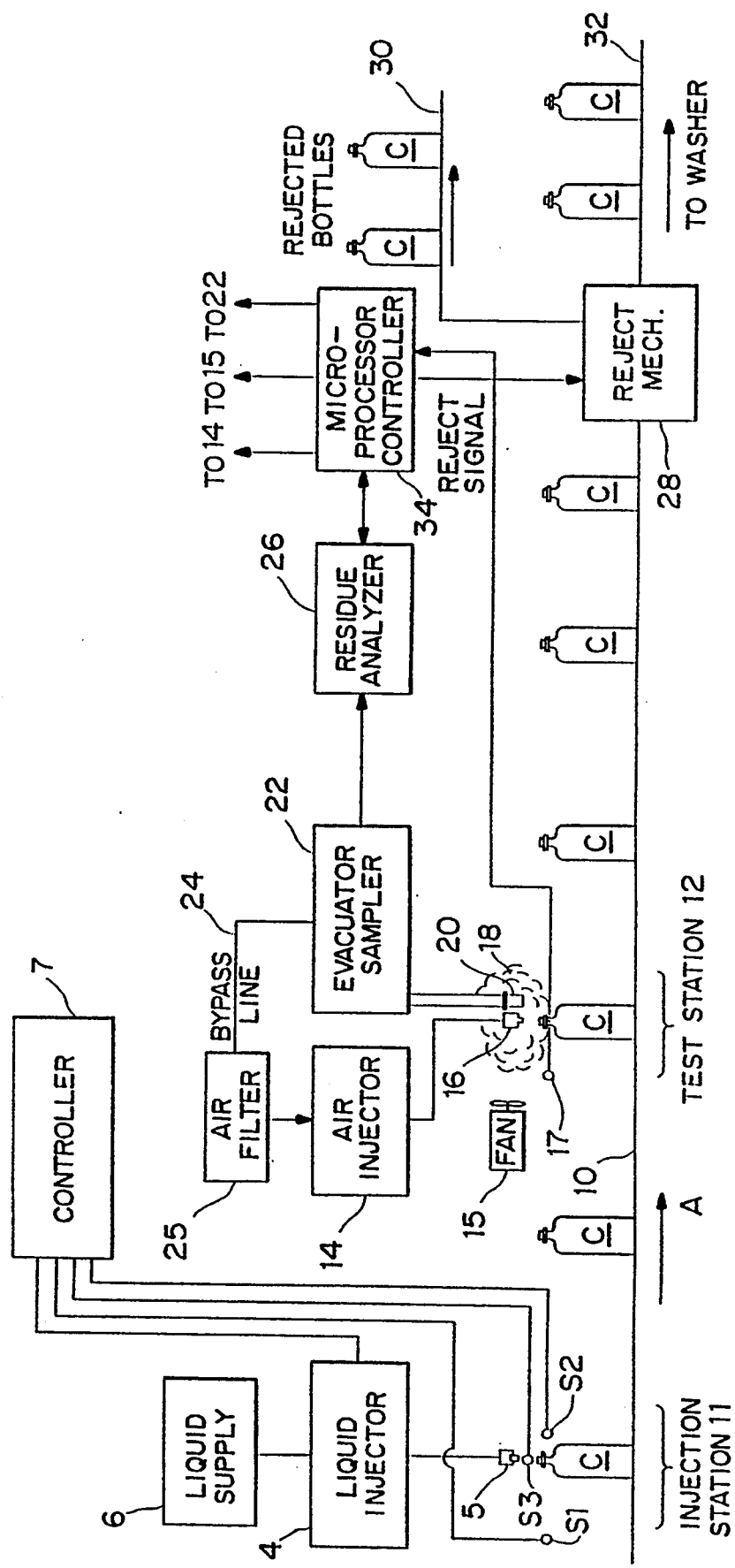
FIG. 1 is a schematic block diagram of the sampling and analyzing system of the present invention illustrating a plurality of containers moving seriatim along a conveyor system past an alkaline injector, and through a test station, reject mechanism and washer station.

In FIG. 1 there is illustrated a conveyor 10 moving in the direction of arrow A having a plurality of uncapped, open-topped spaced containers C (e.g. plastic beverage bottles of about 1500 c.c. volume) disposed thereon for movement seriatim past a liquid injector 4 with a nozzle 5 at an injection station 11 (whose function and operation are described in more detail below) through a test station 12, past a reject mechanism 28 to a washer (not shown), the containers moved by means of a conveyor 32. The contents of containers C typically include air, volatiles of residues of contaminants, if any, and volatiles of any products such as beverages which had been in the containers. An air injector 14 which is a source of compressed air is provided with a nozzle 16 spaced from but aligned with a container C at test station 12. That is nozzle 16 is disposed outside of the containers and makes no contact therewith. Nozzle 16 directs compressed air into containers C to displace at least a portion of the contents of the container to thereby emit a sample cloud 18 to a region outside of the container being tested.

The column of injected air through nozzle 16 into a container C would be typically of the order of about 10 c.c. for bottle speeds of about 200 to 1000 bottles per minute. A rate of 400 bottles per minute is preferable and is compatible with current beverage bottle filling speeds. The desired test rate may vary with the size of the bottles being inspected and filled. Only about 10 c.c. of the container contents would be displaced to regions outside of the bottle to form sample cloud 18.

Also provided is an evacuator sampler 22 which may comprise a vacuum pump or the like coupled to a sampling tube or conduit 20. The tube is mounted near, and preferably downstream (e.g., about 1/16 inch) of the air injector 14 so as to be in fluid communication with sample cloud 18 adjacent to the opening at the top of containers C.

Neither nozzle 16 nor tube 20 contacts the containers C at test station 12; rather both are spaced at positions outside of the containers in close proximity to the openings thereof. This is advantageous in that no physical coupling is required to the containers C, or insertion of probes into the containers, which would impede their rapid movement along conveyor 10 and thus slow down the sampling rate. High speed sampling rates of from about 200 to 500 bottles per minute are possible with the system and method of the present invention. The conveyor 10 is preferably driven continuously to achieve these rates without stopping or slowing the bottles down at the test station.

A bypass line 24 is provided in communication with the evacuator sampler 22 so that a predetermined portion (preferably about 90%) of the sample from cloud 18 entering tube 20 can be diverted through bypass line 24. One purpose of diverting a large portion of the sample from cloud 18 is to reduce the amount of sample passing from evacuator sampler 22 to residue analyzer 26 in order to achieve high speed analysis. This is done in order to provide manageable levels of samples to be tested by the residue analyzer 26. Another purpose for diverting a portion of the sample is to be able to substantially remove all of sample cloud 18 by evacuator 22 from the test station area and divert the excess through bypass line 24. In a preferred embodiment the excess portion of the sample passing through bypass line 24 returned to air injector 14 for introduction into the subsequent containers moving along conveyor 10 through nozzle 16. However, it would also be possible to simply vent bypass line 24 to the atmosphere.

A microprocessor controller 34 is provided for controlling the operation of air injector 14, evacuator sampler 22, residue analyzer 26, a reject mechanism 28 and an optional fan 15. Container sensor 17, including a juxtaposed light source and photodetector, is disposed opposite a reflector (not shown) across conveyor 10. Sensor 17 tells controller 34 when a container arrives at the test station. Optional fan 15 is provided to generate an air blast in the direction of sample cloud 18 to assist in the removal of sample cloud 18 from the vicinity of test station 12 after each container C is sampled. This clears out the air from the region of the test station so that no lingering residues from an existing sample cloud 18 can contaminate the test station area when successive containers C reach the test station for sampling. Thus, sample carryover between containers is precluded. The duty cycle for operation of fan 15 is controlled by microprocessor 34 as indicated diagrammatically in FIG. 1. Preferably fan 15 is continuously operating for the entire time the rest of the system is operating.

A reject mechanism 28 receives a reject signal from microprocessor controller 34 when residue analyzer 26 determines that a particular container C is contaminated with a residue of various undesirable types. Reject mechanism 28 diverts contaminated rejected bottles to a conveyor 30 and uncontaminated, acceptable bottles to a washer (not shown) on a conveyor 32.

Figure 2:
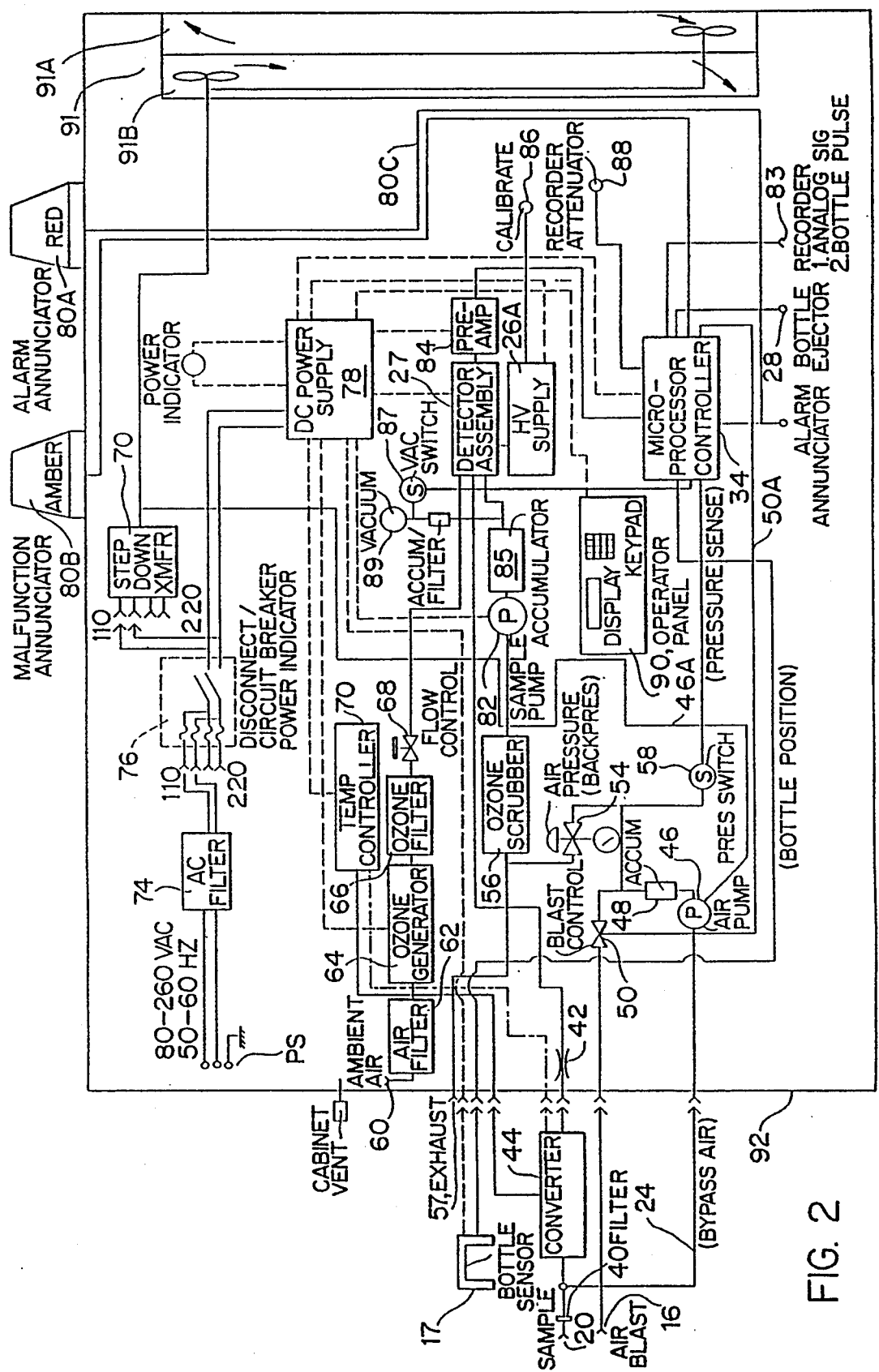
FIG. 2 is a block diagram illustrating a preferred detector system at the test station of FIG. 1.

In FIG. 2 there is illustrated a specific embodiment of a detector system for use with the sampling and analyzing system of FIG. 1 wherein like reference numerals refer to like parts. As illustrated, a nozzle 16 is provided for generating an air blast which passes into a container being inspected. The air passing through nozzle 16 may be heated or unheated it being advantageous to heat the air for some applications. Juxtaposed to the nozzle 16 is sample inlet tube 20 including a filter 40 at the output thereof for filtering out particles from the sample. Suction is provided to tube 20 from the suction side of pump 82 connected through the residue analyzer 26.

A portion of the sample (for example, 90–95% of a total sample flow of about 6000 c.c. per minute), as described in connection with FIG. 1, is diverted through a bypass line 24 by means of connection to the suction side of a pump 46. Pump 46 recirculates the air through an accumulator 48, a normally open blast control valve 50, and back to the air blast output nozzle 16. A backpressure regulator 54 helps control pressure of the air blast through nozzle 16 and vents excess air to exhaust 57. Blast control valve 50 receives control signals through line 50A from microprocessor controller 34 to normally maintain the valve open to permit the flow of air to the nozzle.

Electrical power is provided to pump 46 via line 46A coupled to the output of circuit breaker 76 which is in turn coupled to the output of AC filter 74 and AC power supply PS.

The residue analyzer 26 in the embodiment of FIG. 2 is an analyzer which detects the residue of selected compounds such as nitrogen containing compounds in the containers being inspected by means of a method of chemiluminescence. This type of analyzer is generally known and includes a chamber for mixing ozone with nitric oxide, or with other compounds which react with ozone, in order to allow them to react, a radiation-transmissive element (with appropriate filter), and a radiation detector to detect chemiluminescence from the products of reaction. For example, when NO, produced from heating nitrogen compounds (such as ammonia) in the presence of an oxidant (e.g. oxygen in air), chemically reacts with the ozone, characteristic light emission is given off at predetermined wavelengths such as wavelengths in the range of about 0.6 to 2.8 microns. Selected portions of the emitted radiation of chemiluminescence and its intensity can be detected by a photomultiplier tube.

Accordingly, in the system of FIG. 2 ambient air is drawn in through intake 60 and air filter 62 to an ozone generator 64. Ozone is generated therein, as by electrical discharge into air, and is output through ozone filter 66 and flow control valve 68 to the residue analyzer 26 wherein it is mixed with samples from containers input through intake tube 20, filter 40, converter 44 and flow restrictor 42. The sample from intake tube 20 is passed through a converter 44, such as an electrically-heated nickel tube, in which the temperature is raised to approximately 800° C. to 900° C. before being input to residue analyzer or detector 26. Temperatures as low as 600° C. may be acceptable for converters with other catalysts, and temperatures as high as 1400° C. are also acceptable. When nitrogen-containing compounds such as ammonia and amines are so heated, NO (nitric oxide) is produced, and the nitric oxide is supplied to the analyzer.

A temperature controller 70 supplied with electrical power through a transformer 72 is used to control the temperature of converter 44.

The samples in the residue analyzer (detector assembly) 26 after tests are completed are output through an accumulator 85 and pump 82 to an ozone scrubber 56, and to an exhaust output 57 in order to clear the residue detector for the next sample from the next container moving along the conveyor 10 of FIG. 1. Outputs from residue analyzer 26 relating to the results of the tests are output through a preamp 84 to microprocessor 34 which feeds this information in an appropriate manner to a recorder 83. The recorder 83 is preferably a conventional strip recorder, or the like, which displays signal amplitude vs. time of the sample being analyzed.

The microprocessor 34 may be programmed to recognize, as a "hit" or the detection of a specific residue, a signal peak from a photodetector of the analyzer 26 which is present in a predetermined time interval (based on the sensed arrival of a container at the test station) and amplitude reaches a predetermined magnitude. Alternatively, the microprocessor 34 determines a hit by additional characteristics of the peak such as its slope and the duration of an amplitude of specified magnitude.

The microprocessor controller 34 also has an output to a bottle ejector 28 to reject contaminated bottles and separate them from bottles en route to a washer.

A calibration terminal 86 is provided for residue analyzer 26 for adjusting the high voltage supply 26A associated with the residue analyzer. Also provided is a recorder attenuator input terminal 88 connected to the microprocessor controller 34 for adjusting the operation of the recorder. Analyzer 26 receives electrical power from the high voltage supply 26A.

Additional controls include operator panel 90 including a key pad and display section permitting an operator to control the operation of the residue analyzer 26 in an appropriate fashion.

DC power is supplied to all appropriate components through DC power supply 78 coupled to the output of power supply PS.

An optional alarm enunciator 80A is provided for signaling an operator of the presence of a contaminated container. Alarm enunciator 80A is coupled to the output of microprocessor controller 34 via output control line 80C. A malfunction alarm 80B is also coupled to microprocessor controller 34 for receiving fault or malfunction signals such as from pressure switch 58 or vacuum switch 87 when pressures are outside of certain predetermined limits.

Other safety devices may be provided such as vacuum gauge 89, and back pressure control valve 54 for ensuring proper operation of the system.

Most components of the entire system of FIG. 2 are preferably enclosed in a rust-proof, stainless steel cabinet 92. The cabinet is cooled by a counter-flow heat exchanger 91 having hermetically separated sections 91A and 91B in which counter air flow is provided by appropriate fans.

Potential contaminants in beverage bottles include nitrogen compounds and the system and method illustrated in FIGS. 1 and 2 can be utilized to detect the presence of nitrogen compounds in those beverage bottles. Among these are proteins, free amino acids, ammonium ions, acid salts of ammonia and amines, and free ammonia. Nitrogen chemiluminescence provides a selective, sensitive, rapid and relatively simple approach to detecting the presence of nitrogen compounds. Organic nitrogen compounds and ammonia can be detected by chemiluminescence after conversion of nitrogen therein to nitric oxide (NO). The system of FIG. 2 converts nitrogen compounds to NO, mixes NO with ozone and then detects the chemiluminescence generated.

It is a discovery of the present invention that the addition of sodium carbonate ($Na_2CO_3$) significantly enhances the release of volatiles such as ammonia and their amines from their salts—e.g., ammonium salts such as ammonium phosphate and ammonium citrate, and amine salts such as those produced from amino acids. This is due to the shift in the pH of the sample from or slightly basic to highly basic. The change in pH results in an instantaneous liberation of vapors of ammonia and amines from their acid salts. This mechanism greatly enhances the likelihood that a gas-phase detection system such as a chemiluminescence analyzer will detect the presence of ammonium and amine salts present in a container.

Preferably the chemical added to the bottles will raise the pH of the sample to 9 or greater, most preferably to 10.5 or greater.

$Na_2CO_3$ is the preferred chemical because it is inexpensive and non-hazardous. Also, it is not harmful to the plastics from which beverage bottles are typically fabricated. Alternative chemical additives to $Na_2CO_3$ are, tri-sodium phosphate ($Na_3PO_4$), tri-potassium phosphate ($K_3PO_4$), and hydrated forms of $Na_2CO_3$ which possess the same advantages and characteristics as $Na_2CO_3$.

Less desirable, but effective, chemical additives for raising the pH to a level for enhancing the release of vapors of ammonia and amines are KOH and NaOH. However, these chemicals are more expensive than $Na_2CO_3$, are caustic, and may be harmful to materials such as plastic. These additives typically raise the pH of the sample to about 14.

The chemical additive, preferably $Na_2CO_3$, is introduced into bottles C in the system of FIG. 1 upstream of test station 12 by one or more liquid injectors such as the injector 4 shown in FIG. 1 which is supplied with liquid (e.g. $Na_2CO_3$) by a liquid supply 6 and operated under control of an electronic controller 7. (Alternatively, the injector may be controlled by microprocessor controller 34). The sodium carbonate introduced is prepared as an aqueous solution of from about 1 to 20 percent by weight—preferably about 5 percent—and about one to ten cubic centimeters of the solution are introduced into bottles C.

The $Na_2CO_3$ solutions may be sprayed continuously into bottles C, or injected as a pulsed jet from a jet pump in synchronism with the movement of containers C through test station 12. Any excess solution not entering bottles C is preferably collected and recirculated for injection into the bottles to avoid waste.

Solutions of sodium carbonate, or alternative chemical additives, may be prepared by simply adding the chemical as a powder to water while stirring. Sufficient powder is dissolved to provide a solution of the desired strength e.g. a five percent solution of $Na_2CO_3$ and water.

Test results indicate that the addition of $Na_2CO_3$ to bottles being tested substantially increases the ability of the chemiluminescence detection system of FIG. 2 to detect vapors of ammonia and amines released from nitrogen compounds such as ammonium salts. In fact, without sodium carbonate, ammonium salts in bottles at typical levels may be indistinguishable from background signals. With sodium carbonate, detection is virtually certain since detection signals may increase by several orders of magnitude.

Figure 3:
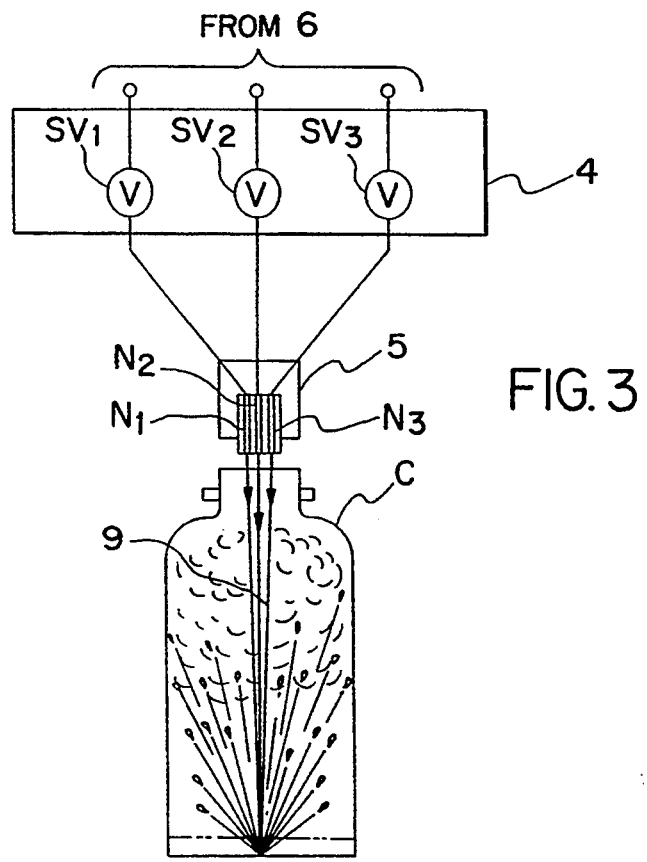
FIG. 3 is an enlarged view of a preferred embodiment of an alkaline injector of FIG. 1.
Figure 4:
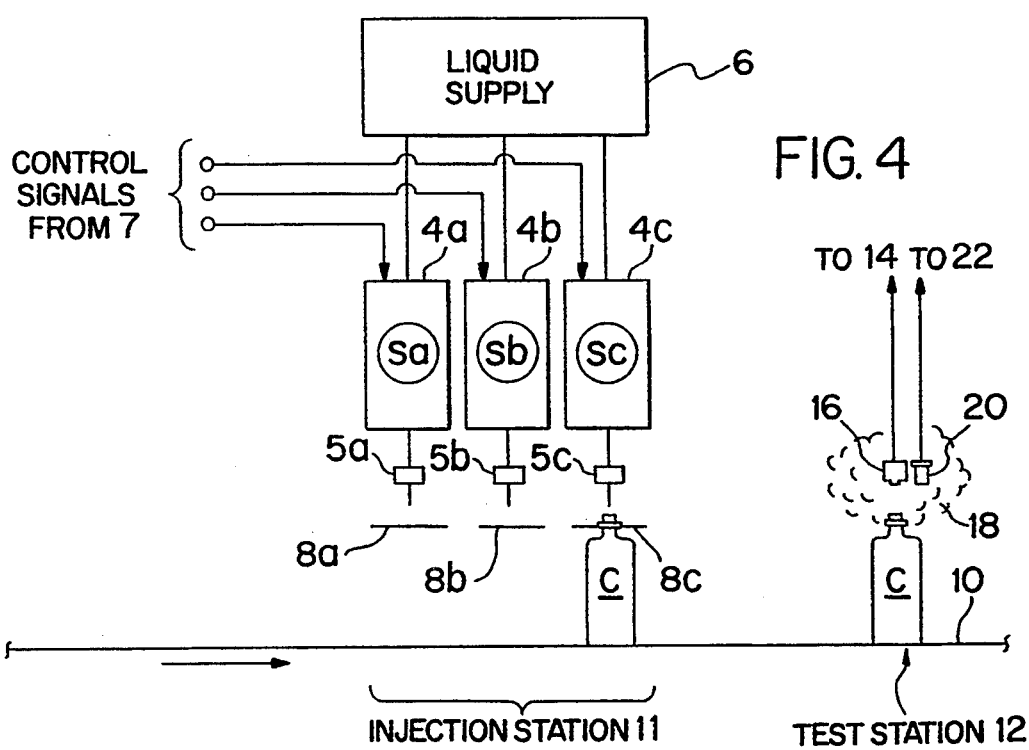
FIG. 4 is a block diagram illustrating another embodiment of the alkaline injector including three injector assemblies in series.
Figure 7:
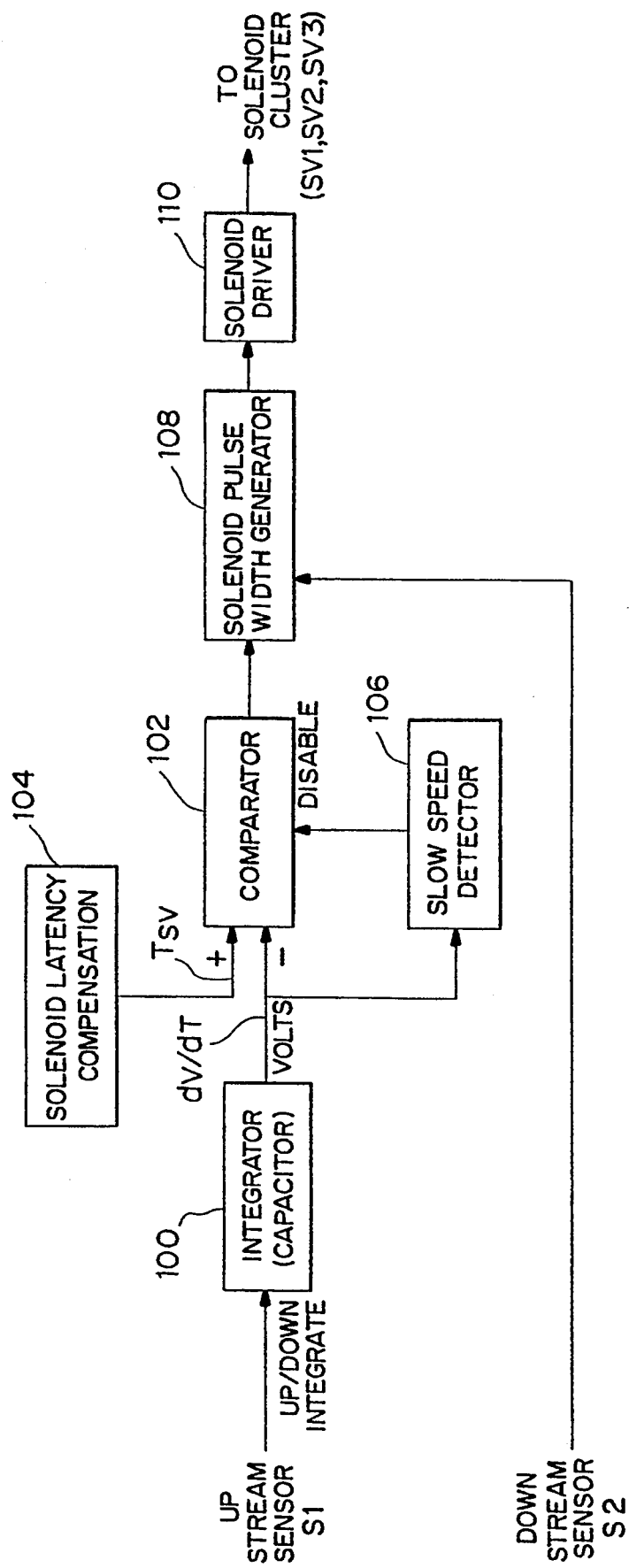
FIG. 7 is a block diagram of an analog controller for controlling injection and ensuring that liquid from the injectors does not spill over the outside, or between the bottles.

FIGS. 3 and 4 illustrate preferred embodiments of the liquid injection system illustrated in the upstream (left) portion of FIG. 1. FIG. 3 is an enlarged view of a portion of the system illustrating how sodium carbonate injector 4 with its associated nozzles 5a, 5b, and 5c sprays a plurality of narrow streams of sodium carbonate 9 into a container C in order to displace the vapors of ammonia or amines to be detected in a manner to be described more fully hereinafter. FIG. 4 is a schematic diagram of a portion of the conveyor line of FIG. 1 illustrating a plurality of injector mechanisms 4a, 4b, 4c, in tandem.

The injector 4 of FIG. 3, and the injectors 4a, 4b, 4c of FIG. 4, spray sodium carbonate solution from a pressurized supply 6 into bottles C through the open tops thereof. Each injector mechanism is timed to spray only when the top opening defined by the surrounding neck portion of a bottle C is under its associated nozzles. Thus, substantially no sodium carbonate solution spills over the outside of, or between, bottles C.

To allow for different speeds of travel of bottles, the injection system senses the speed of a bottle passing sensors such as the sensor S1 illustrated in FIG. 1. Each of the sensors S1, S2, S3, and 17 shown in FIG. 1, and the groups of sensors 8a, 8b, and 8c illustrated schematically in FIG. 4, are optical interrupters. They may be of the reflective type and include a photodetector positioned to detect light from a source (adjacent to the photodetector) which is directed across the conveyor 10 and reflected from a reflector (not shown) mounted opposite the sensor. Alternatively, they may be of the transmissive type and include an emitter and detector on opposite sides of the conveyor 10. The light beam is interrupted by the leading edge of the neck of the bottle C and then detected again as the trailing edge of the neck passes the light source of the sensor.

The injector 4 is preferably positioned about 5/3 "neck widths" (about 5/3 inch for typical bottle neck—O.D. of 1 inch, I.D. of 0.8 inch) downstream of the light beam in time so that, at the fastest conveyor speed of, for example, 400 bottles per minute, sodium carbonate solution will only be sprayed during an interval over which the opening of the bottle will be below the nozzle 5 of the injector 4. Therefore, for "unspaced" bottles—no gap between adjacent bottles—of about 3.6 inches maximum diameter, there is an "active" window of about 20-25 milliseconds in which solution is sprayed into a bottle C. A somewhat shorter interval may be used to provide a safety margin against spillage.

As shown in detail in FIG. 3, the injector 4 preferably includes three nozzles 5a, 5b, 5c, which are preferably stainless steel hypodermic needle tubes of tip diameters 0.067 inches, brazed together and mounted about one-quarter to one-half inch above the top of bottles C passing therebelow. Each of the hypodermic needle tubes N1, N2 and N3 is connected to a solenoid valve—i.e., the valves SV1, SV2, SV3, respectively. Preferably the solenoid valves have orifice sizes of $\frac{1}{8}$ inch behind which the sodium carbonate solution is maintained under pressure of about 70 psi by a suitable (diaphragm) pump included within sodium carbonate supply 6.

The valves SV1, SV2, SV3 are synchronized so that solution flows simultaneously from all three tubes, N1, N2, and N3. Control signals are provided to the solenoid valves from sensor S1 via electronic controller 7 (or microprocessor 34). The tubes 5a, 5b, 5c emit three high speed narrow streams 9 which enter the bottle C and coalesce therein. Three nozzles are used in order to get a narrow, high flow, high speed stream. Although a single nozzle would work, it may produce a jet of larger diameter than desired and fail to achieve as much splashing and associated displacement of the vapors to be detected.

Each nozzle 5a, 5b, 5c typically dispenses about ½ cc. in the 20-25 millisecond time of the "active" window in which valves SV1, SV2, SV3 are open.

FIG. 3 illustrates one nozzle assembly including the three juxtaposed nozzles 5a, 5b, 5c. However, more than one injector assembly 4 may be utilized for redundancy, and in order to supply a sufficient amount of sodium carbonate solution to each bottle. Such a system is illustrated in FIG. 4 wherein three injector assemblies 4a, 4b, and 4c, each identical in construction to injector assembly 4 of FIG. 3, are disposed in series closely spaced one after the other on the conveyor line A. Each injector assembly 4a, 4b, 4c, has an associated sensor group 8a, 8b, and 8c, with multiple sensors (e.g. 3) in each group, and each is connected to an appropriate group of solenoid valve assemblies Sa, Sb, Sc. Each of the solenoid valve assemblies includes three solenoid valves SV1, SV2, SV3, as illustrated in FIG. 3. Each of the injector assemblies 4 dispenses about 1.5 cc. of solution of sodium carbonate since each respective nozzle thereof dispenses ½ cc. Since it is desirable to dispense in excess of 1.5 cc. of solution into each bottle, the series or tandem arrangement of FIG. 4 including three injector mechanisms 4a, 4b, 4c, provides for the injection of 4.5 cc. of solution to each bottle. Another advantage of providing three injectors mechanisms in tandem is that each one displaces a portion of the vapors to be detected within the container from the bottom towards the top portion thereof, which is advantageous as described hereinafter.

If vigorous or high speed injection is employed into the container C, the injectors 4 can be located quite close, as, for example, as close as 1½ feet, upstream of the test station 12 at which sampling and analysis occur. This is important in minimizing conveyor length, an advantage especially when adding the overall apparatus to existing conveyor lines. When sodium carbonate is vigorously injected, streams 9 hit the bottom of the bottle, or side portions near the bottom, and cause splashing of a portion of the contents to about half bottle height, liquid then being observed to run back down the sides. This agitation and splashing is significant in rapidly getting vapors of ammonia and/or amines from bottom portions of the bottle to a point within its upper region such that accurate sampling and detection can occur soon after injection. Also, it is not necessary to add sufficient sodium carbonate to raise the pH of the entire contents of the bottle to 9 or above, since the vigorous mixing and splashing will at least locally produce some ammonia and/or amine vapors which may be sampled and detected.

It should be understood, however, that even though short distances between the sodium carbonate solution injector assemblies and test station 12 seem to be desirable, that the injector can be disposed 20 or 30 feet or greater upstream of the detector station 12 and still work quite well.

FIGS. 5 to 8 illustrate control systems and their use in rapidly injecting small amounts of liquid into bottles as described above moving at constant or variable speeds and spacings. These control systems ensure that none of the liquid spills over the outside of or between, the containers.

FIG. 5 is a top diagrammatic view, showing a bottle C with opening Co moving from left to right on the conveyor 10 through optical beams Flag1 and Flag2 established between sensors S1 and S2 and the jet(s) J from the nozzles N1, N2, N3. First, the leading edge of the bottle breaks light beam Flag1 at time T1. Next, the trailing edge of the bottle passes Flag1 at time T2 and the light beam is restored and again detected by sensor S1. The time interval T2-T1 between these two transitions is used to measure the speed of the bottle and predict the correct time to turn on the liquid jets.

The distance between sensors S1 and S2 is approximately 1.5 inches, and the outer diameter of the bottle neck defining opening Co is X1, approximately 1 inch. The jet is timed to begin when the jet nozzle is positioned just inside the bottle opening, near the leading edge. This maximizes the time available to inject liquid into the bottle C.

The solenoid valves SV1, SV2, SV3 have a consistent lag time, designated $T_{SV}$, for example, 14 milliseconds, between electronic switching and emergence of the liquid jet. The valves should therefore be switched on $T_{SV}$ milliseconds before the bottle C arrives in the optimal position.

FIG. 6 further illustrates the control system operation. Let X2 be the distance the bottle must travel between leaving the position of Flag1 and arriving at the optimal position for initiation of the liquid jet. The time required to move this distance is equal to $X2*(T2-T1)/X1$. Thus, the solenoid valve should be switched on at time $T2+X2,(T2-T1)/x1-T_{SV}$.

If the bottle C is moving very slowly, a default timer times out before T2. In this case, Flag2 is used to switch on the valve when the leading edge of the bottle C reaches sensor S2, which is positioned about 0.25 inches downstream of the nozzles N1, N2, N3 producing jet(s) J.

The control system functions described above can be implemented using either analog or digital circuits in the controller 7. In the analog circuit of FIG. 7 a capacitor 100 is charged at constant dV/dT between T1 and T2, and is then discharged at a proportional rate. The time required to discharge the capacitor 100 is proportional to the time required to charge it, so that the circuit responds to the speed of the bottle on the conveyor. A comparator 102 is used to switch on the valves SV1, SV2, SV3 when the capacitor 100 has discharged to a voltage equal to $dV/dT*T_{SV}$. The valves are thereby switched on $T_{SV}$ milliseconds early by solenoid latency compensator 104, so that the bottle will be in position when the liquid jet emerges. A separate timer, solenoid pulse width generator 108 is used to fix the on-time of the solenoid valves, typically about 20 milliseconds. Pulse width generator 108 is turned on by comparator 102 or by down stream sensor S2. Generator 108 controls solenoid driver 110. If the bottle is moving very slowly, the slow speed is sensed by slow speed detector 106, the op amp within comparator 102 will saturate prior to T2. If the op amp saturates, S2 is used to switch on the valves via generator 108 and driver 110.

Figure 8:
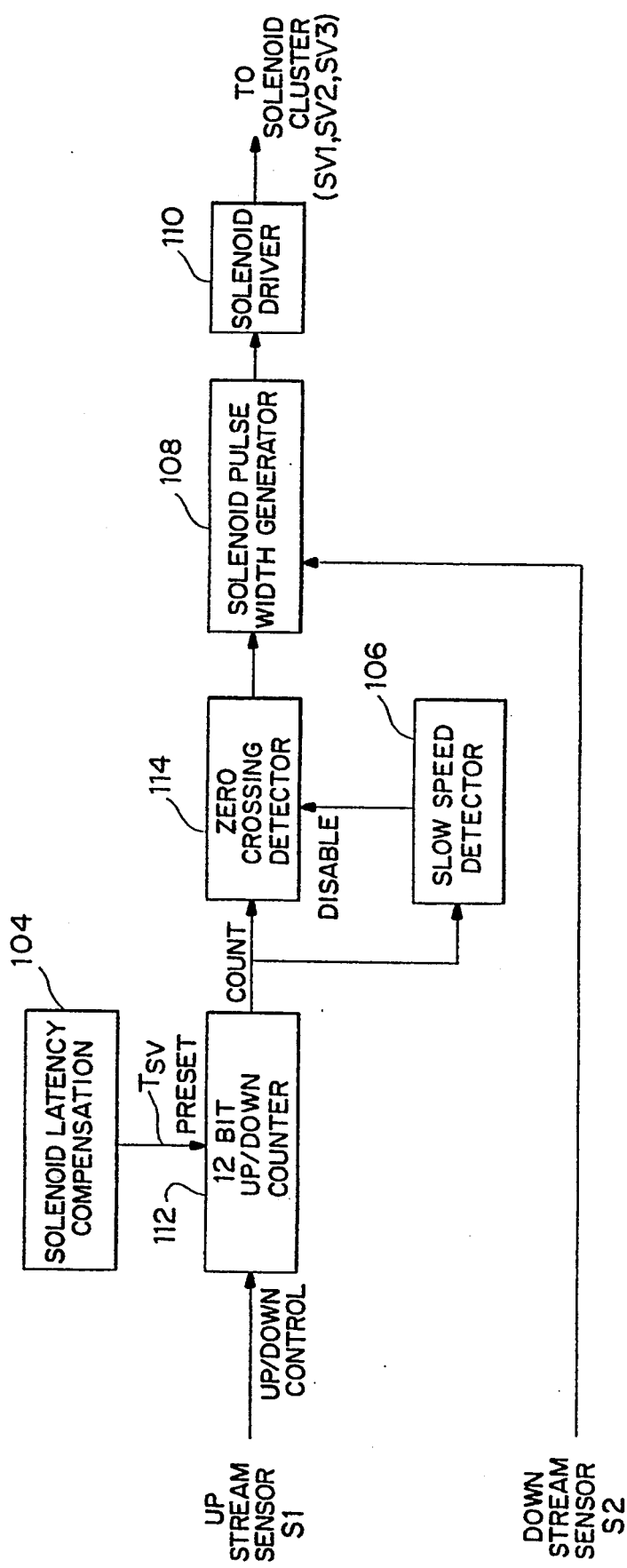
FIG. 8 is a block diagram of a digital controller for performing the same function as the controller of FIG. 7.

In the digital implementation of FIG. 8, a 12 Bit Up/-Down counter 112 is initially set to a value proportional to $T_{SV}$. An oscillator within counter 112 provides a clock signal, for example, at 0.125 millisecond intervals. From T1 to T2, the counter is allowed to count down, reaching a value less than zero. After T2, the counter 112 counts up. When the counter reaches zero this value is detected by zero crossing detector 114, the values SV1, SV2, SV3 are switched on. The on-time of the solenoid valves is fixed by a separate counter driven by the same clock. In the case of a slowly-moving bottle, the down-counter reaches a preset negative value before T2 occurs which is sensed by slow speed detector 106, and S2 is enabled.

Optionally, a third optical sensor may be used to detect the presence of the liquid jet, to detect solenoid valve failure and continuous spewing of liquid through the nozzles. A suitable detector for sensing the condition of the third optical beam—e.g., sensor S3 positioned at the axial (conveyor) location of the nozzle(s) 5 and slightly above the top of each container C moving along the conveyor 10, as illustrated in FIG. 1, can of course be connected to the controller 7 (or microprocessor controller 34) to provide these status signals of the solenoid valves thereto. Controller 7, processes these signals and generates appropriate warning signals.

The solution of sodium carbonate, as described hereinbefore, is preferably 5% by weight (which is also about 5% by volume) dissolved in water. Although higher amounts may be used, above about 7% may be undesirable because that is about the solubility limit of sodium carbonate at temperatures near freezing. A "humectant" such as glycerol may be added to the solution, in amounts roughly similar to the sodium carbonate, to make the solution into a "non-drying" solution so as to prevent problems with machinery (e.g., the conveyors) which could occur if the sodium carbonate were to get into unintended locations and dry to crystalline form at which point it would be somewhat abrasive.

Another aspect of the present invention is to provide reliable methods for testing the operation of the systems of FIGS. 1 and 2. It is important to know, for example, if the detection system is functioning properly to detect ammonium salts and amine salts assuming their presence in the bottles. It is also important to be able to verify that chemical additives such as $Na_2CO_3$ are being properly injected into containers C.

The ability of the system to detect free ammonia and amines, assuming the presence of ammonium and amine salts, may be checked during a calibration process by injecting solutions of a known amine salt into containers C for example, by means of an injector (not shown) positioned upstream of the alkaline injector 4 and above the containers C. Salts such as ammonium phosphate, ammonium chloride, ammonium acetate or ammonium sulfate could be used. Since it is known that these chemicals will release free ammonia in known quantities, the proper operation of the detection system of FIG. 2 can be verified.

As explained above, it is also important to know if proper amounts of $Na_2CO_3$ are being injected into containers C. This can be verified by injecting a clear dye into containers C which would change color at a pH of about 9 or greater. Since the carbonate changes the sample pH to 9 or greater, this change in color would likely indicate the presence of the carbonate and the proper operation of the injection mechanism into containers C.

It should be noted that the absence of a color change for the pH dye could still be accompanied by a "hit" or reject signal from the system. However, this "hit" signal could be caused by detection of contaminants in the sample other than amine salts or ammonium salts—e.g., gasoline. Therefore, the use of a pH dye to verify the presence of $Na_2CO_3$ is desirable.

Preferred embodiments of the invention having been described, it will be obvious that they may be varied in many ways. For example, other high speed analyzers for ammonia and amines, such as electron capture detectors, and infrared detectors, may be suitable in place of the chemiluminescence analyzer described with reference to FIG. 2.

In addition, the materials to be inspected are not limited to substances in containers. For example, the method and system of the present invention could be used to detect volatiles adsorbed in shredded strips or flakes of resins, or plastic stock to be recycled for manufacturing new plastic beverage bottles. This shredded or flaked plastic stock could be placed in baskets, buckets or other types of containers disposed thereon and inspected in batches.

Such variations are not to be regarded as a departure from the spirit and scope of the invention, and all such modifications as would be obvious to one skilled in the art are intended to be included within the scope of the following claims.

What is claimed is:

1. A method of sampling and determining presence of ammonium salts and amine salts in a container comprising the steps of:
    adding sodium carbonate to the container to enhance liberation of vapors of ammonia or an amine, or both from any ammonium salts and amine salts therein;
    displacing a portion of contents of the container including said vapors to form a sample cloud at regions outside of the container adjacent an opening thereof;
    mixing a portion of the sample cloud with a chemical reactant to generate a chemical reaction with said vapors of ammonia or amine which causes chemiluminescence; and
    analyzing radiation from said chemiluminescence to determine the presence or absence of ammonium salts or amine salts.

2. The method of claim 1 wherein said step of displacing includes injecting fluid into an opening in said container to form said sample cloud.

3. The method of claim 1 wherein the sodium carbonate added is an aqueous solution containing about one to twenty percent by weight of sodium carbonate.

4. The method of claim 3 further including the step of heating a portion of said sample cloud before mixing the cloud with the chemical reactant.

5. The method of claim 1 wherein said portion of the cloud is heated to a temperature within the range from about 600° to 1400° C.

6. A method of sampling and determining presence of ammonium salts and amine salts in a container comprising the steps of:
    adding sodium carbonate to the container to enhance liberation of vapors of ammonia or an amine, or both from any ammonium salts and amine salts therein;
    displacing a portion of contents of the container including said vapors to form a sample cloud at regions outside of the container adjacent an opening thereof; and analyzing a sample including the vapors to determine the presence or absence of ammonium salts or amine salts therein.

7. The method of claim 6 wherein said step of displacing includes injecting fluid into an opening in said container to form said sample cloud.

8. The method of claim 6 wherein the sodium carbonate added is an aqueous solution containing about one to twenty percent by weight of sodium carbonate.

9. A method of sampling and determining presence of ammonium salts and amine salts in a container comprising the steps of:
  adding a chemical additive from the group consisting of sodium carbonate, hydrated sodium carbonate, sodium tri-phosphate, potassium tri-phosphate and mixtures thereof to the container to enhance liberation of vapors of ammonia or an amine, or both from any ammonium salts and amine salts therein;
  displacing a portion of contents of the container including said vapors to form a sample cloud at regions outside of the container adjacent an opening thereof;
  mixing a portion of the sample cloud with a chemical reactant to generate a chemical reaction with said vapors of ammonia or amine which causes chemiluminescence; and
  analyzing radiation from said chemiluminescence to determine the presence or absence of ammonium salts or amine salts therein.

10. The method of claim 9 wherein said step of displacing includes injecting fluid into an opening in said container to form said sample cloud.

11. The method of claim 9 wherein the sodium carbonate added is an aqueous solution containing about one to twenty percent by weight of sodium carbonate.

12. The method of claim 11 further including the step of heating a portion of said sample cloud before mixing the cloud with the chemical reactant.

13. The method of claim 12 wherein said portion of the cloud is heated to a temperature within the range from about 600° to 1400° C.

14. A method of sampling and determining presence of ammonium salts and amine salts in a container comprising the steps of:
  adding a chemical additive from the group consisting of sodium carbonate, hydrated sodium carbonate, sodium tri-phosphate, potassium tri-phosphate and mixtures thereof to the container to enhance liberation of vapors of ammonia or an amine, or both from any ammonium salts and amine salts therein;
  displacing a portion of contents of the container including said vapors to form a sample cloud at regions outside of the container adjacent an opening thereof; and
  analyzing a sample including the vapors to determine the presence or absence of ammonium salts or amine salts therein.

15. The method of claim 14 wherein said step of displacing includes injecting fluid into an opening in said container to form said sample cloud.

16. The method of claim 14 wherein the sodium carbonate added is an aqueous solution containing about one to twenty percent by weight of sodium carbonate.

17. A method of sampling and determining presence of ammonium salts and amine salts in a container comprising the steps of:
  injecting an aqueous solution of a chemical additive into the container through an opening therein to enhance liberation of vapors of ammonia or an amine, or both from any ammonium salts and amine salts therein, said aqueous solution being injected at a sufficient velocity to displace a portion of vapors so liberated towards a top region of said container;
  thereafter injecting a fluid through the opening to displace a portion of the vapors in the top region to regions outside of said container to form a sample cloud outside of the container adjacent the opening thereof; and
  analyzing a sample of the vapors in the sample cloud to determine the presence or absence of ammonia or amines therein so as to determine the presence or absence of ammonium salts or amine salts in said container.

18. The method of claim 17 including moving a plurality of said containers seriatim through at least one additive injection station at which said aqueous solution of chemical additives is injected, and through a test station at which said fluid is injected, said at least one additive station being spaced a sufficient distance upstream from said test station to permit said displaced portion of the vapors of ammonia or amines to reach a top region of the container by the time the container arrives at the test station.

19. The method of claim 18 moving said containers through a plurality of spaced additive stations disposed in series upstream of the test station and injecting said aqueous solution into each container at each additive station.

20. The method of claim 19 wherein the step of injecting aqueous solution includes forming the aqueous solution into a plurality of separate streams and directing the separate streams through the opening in the container.

21. The method of claim 17 wherein the step of injecting aqueous solution includes forming the aqueous solution into a plurality of separate streams and directing the separate streams through the opening in the container.

22. The method of any of claims 17, 18, 19, 20 or 21 wherein the chemical additive is selected from the group consisting of sodium carbonate, hydrated sodium carbonate, sodium tri-phosphate, potassium tri-phosphate and mixtures thereof.

23. The method of claim 22 comprising the further steps of mixing the sample from the sample cloud with a chemical reactant to generate a chemical reaction with the sample to generate chemiluminescence; and
  analyzing radiation from the chemiluminescence to determine the presence or absence of said ammonium or amine salts.

24. A system for sampling and determining presence of ammonium salts and amine salts in a container comprising:
  means for injecting an aqueous solution of a chemical additive into the container through an opening therein to enhance liberation of vapors of ammonia or an amine, or both from any ammonium salts and amine salts therein, said aqueous solution being injected at a sufficient velocity to displace a portion of vapors so liberated to a top region of said container;
  means for injecting a fluid through the opening to displace a portion of said liberated vapors in the top region to regions outside of said container to form a sample cloud outside of the container adjacent the opening thereof; and means for analyzing a sample of the vapors in the sample cloud to determine the presence or absence of ammonia or amine therein so as to determine the presence or absence of ammonium salts or amine salts in said container.

25. The system of claim 24 wherein said means for injecting aqueous solution and said means for injecting fluid are mounted at an additive injection station and a test station, respectively, adjacent to a conveyor operable to move a plurality of containers seriatim through said injection station and then through said test station, said additive station being spaced a sufficient distance upstream from said test station to permit liberated vapors of ammonia or amines to reach the top region of the container by the time the container arrives at the test station.

26. The system of claim 25 wherein the means for injecting aqueous solution includes means for forming the aqueous solution into a plurality of separate streams and directing the separate streams through the opening in the container.

27. The system of claim 24 wherein the means for injecting aqueous solution includes means for forming the aqueous solution into a plurality of separate streams and directing the separate streams through the opening in the container.

28. The system of claim 24 further comprising means for mixing the sample from the sample cloud with a chemical reactant to generate a chemical reaction with the sample to generate chemiluminescence; and means for analyzing radiation from the chemiluminescence to determine the presence or absence of said ammonium or amine salts.

* * * * *